US00PP26568P2

(12) United States Plant Patent
Trees

(10) Patent No.: US PP26,568 P2
(45) Date of Patent: Apr. 5, 2016

(54) ***ROSA* PLANT NAMED 'SFROSA154'**

(50) Latin Name: *Rosa hybrida*
Varietal Denomination: SFROSA154

(71) Applicant: Scott C. Trees, Arroyo Grande, CA (US)

(72) Inventor: Scott C. Trees, Arroyo Grande, CA (US)

(73) Assignee: SUNRISE FARMFLOWERS, LLC, Arroyo Grande, CA (US)

( * ) Notice: Subject to any disclaimer, the term of this patent is extended or adjusted under 35 U.S.C. 154(b) by 78 days.

(21) Appl. No.: 14/121,314

(22) Filed: Aug. 19, 2014

(51) Int. Cl.
*A01H 5/00* (2006.01)

(52) U.S. Cl.
USPC ..... Plt./106

(58) Field of Classification Search
USPC ..... Plt./106
See application file for complete search history.

*Primary Examiner* — Annette Para
(74) *Attorney, Agent, or Firm* — Penny J. Aguirre

(57) ABSTRACT

A new cultivar of shrub rose, 'SFROSA154', that is characterized by its compact, upright and branching plant habit, its semi-double flowers with eight to ten petals that are salmon pink in color, its dark green foliage, its cold hardiness at least to U.S.D.A. Zone 6, and its tolerance to powdery mildew and rust in California trials.

2 Drawing Sheets

Botanical classification: *Rosa hybrida.*
Variety denomination: 'SFROSA154'.

BACKGROUND OF THE INVENTION

The present invention relates to a new and distinct cultivar of *Rosa hybrida*. The new cultivar will be referred to hereafter by its cultivar name, 'SFROSA154'. 'SFROSA154' is a new cultivar of shrub rose grown for use as a landscape shrub.

The new cultivar of shrub rose is a selection from a controlled breeding program conducted by the Inventor in Arroyo Grande, Calif. with an objective to create new shrub rose cultivars with disease resistance, ever blooming habits, unique brightly colored flowers that can be readily propagated on their own roots.

The new variety of shrub rose, 'SFROSA154', was selected by the Inventor from amongst seedlings derived from open pollination of 'WEKbepmey' (U.S. Plant Pat. No. 19,144) in 2010. 'SFROSA154' was selected as a single unique plant in May of 2011.

Asexual propagation of the new cultivar was first accomplished by stem cuttings in Arroyo Grande, Calif. in August of 2011 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'SFROSA154' as a new and unique cultivar of shrub rose.

1. 'SFROSA154' exhibits a compact, upright, branching plant habit.
2. 'SFROSA154' exhibits semi-double flowers, with eight to ten petals, that are salmon pink in color.
3. 'SFROSA154' exhibits dark green foliage.
4. 'SFROSA154' exhibits cold hardiness at least to U.S.D.A. Zone 6.

5. 'SFROSA154' exhibits tolerance to powdery mildew and rust in California trials.

The female parent of 'SFROSA154', 'WEKbepmey', differs from 'SFROSA154' in having flowers that are bright golden yellow in color, in having a more vigorous growth rate, in having a taller more upright plant habit, in having flowers with 25 to 30 petals. 'SFROSA154' can also be compared to plants of the shrub rose cultivars 'Flower Carpet' (U.S. Plant Pat. No. 7,282) and 'Radral' (U.S. Plant Pat. No. 19,803). 'Flower Carpet' is similar to 'SFROSA154' in having semi-double flowers and in having a compact plant habit. 'Flower Carpet' differs from 'SFROSA154' in have a more vigorous growth rate, in having a more trailing plant habit, in having flowers that are hot pink in color, and in having glossier foliage. 'Radral' is similar to 'SFROSA154' in having a shrub-like habit and semi-double flowers that are salmon pink in color. 'Radral' differs from 'SFROSA154' in being cold hardy to U.S.D.A Zone 4, in having a more vigorous growth rate, and in having flower petals that are more rounded in shape.

BRIEF DESCRIPTION OF THE DRAWINGS

The accompanying colored photographs illustrate the overall appearance and distinct characteristics of the new shrub rose. The photographs were taken of a one year-old plant as grown outdoors in a one-gallon container in Arroyo Grande, Calif.

The photograph in FIG. 1 provides a side view of the plant habit of 'SFROSA154'.

Figure 1:
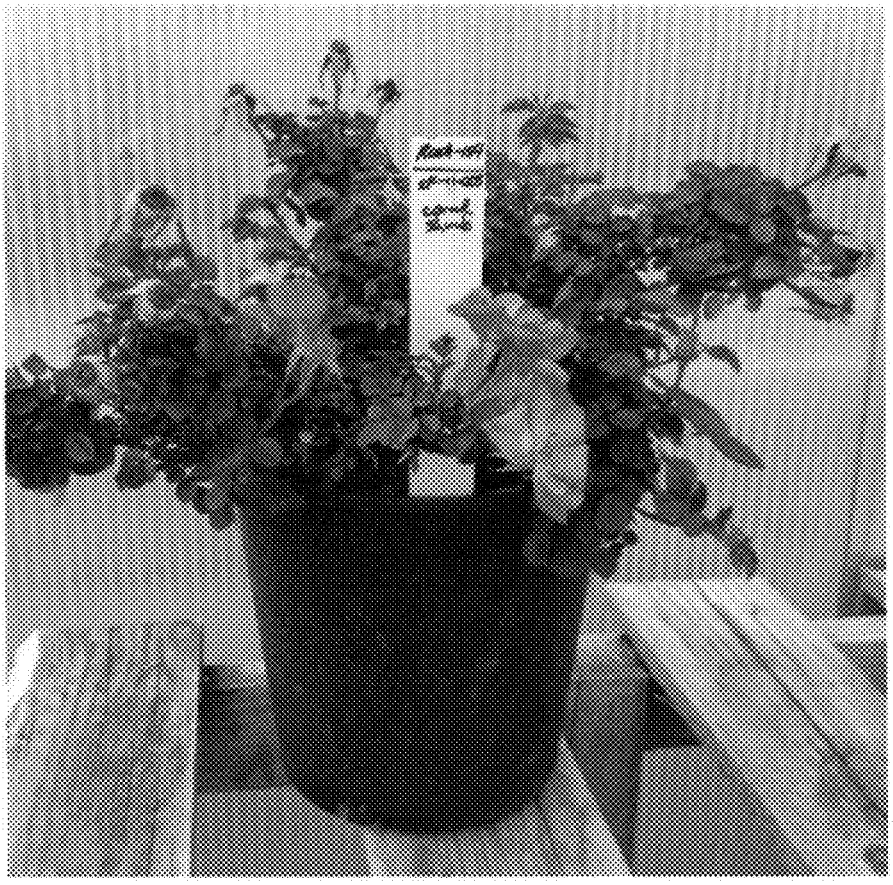
Figure 2:
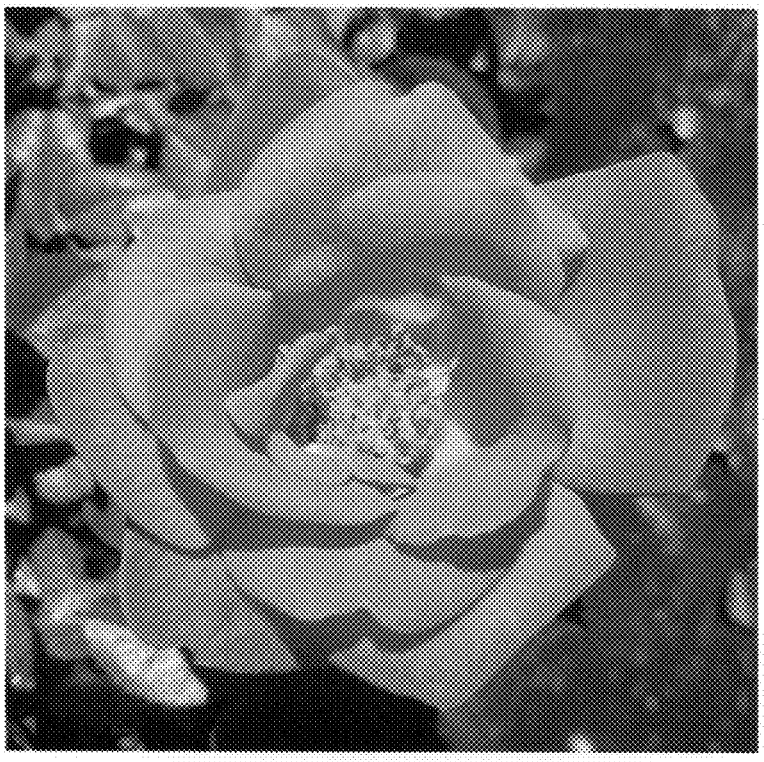

The photograph in FIG. 2 provides a close-up view of a mature flower of 'SFROSA154'.

Figure 3:
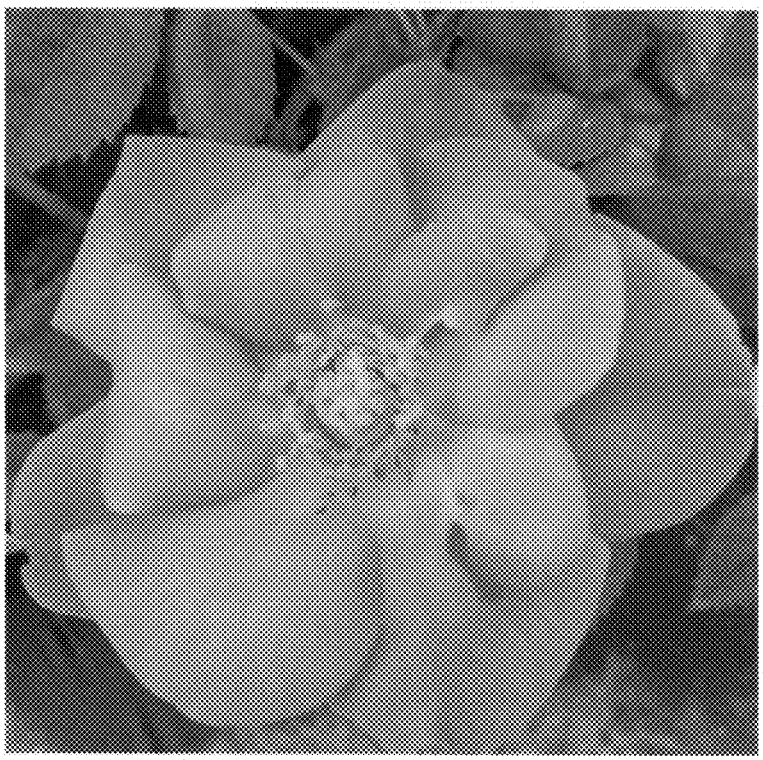

The photograph in FIG. 3 provides a close-up view of an aging flower of 'SFROSA154'.

The colors in the photographs are as close as possible with the photographic and printing technology utilized and the color values cited in the detailed botanical description accurately describe the colors of the new shrub rose.

DETAILED BOTANICAL DESCRIPTION

The following is a detailed description of one year-old plants of the new cultivar as grown outdoors in 2-quart containers in Arroyo Grande, Calif. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit.*—Year-round continuous bloom in California from June to first frost in mid-western, northeastern, and southeastern US.

*Plant type.*—Deciduous shrub.

*Plant habit.*—Compact, upright, and branching.

*Height and spread.*—Up to 91 cm in height and an average of 60 cm in width.

*Cold hardiness.*—At least to U.S.D.A. Zone 6.

*Diseases and pests.*—Has shown tolerance to powdery mildew and rose rust in trials in California.

*Propagation.*—Stem cuttings.

*Growth rate.*—Slow to moderate.

Branch description:

*Stem color.*—Young; 144A, suffused with 178A, maturing; 144A, mature wood; ridges of 177A to 177C.

*Stem surface.*—Young; glabrous, mature; slightly glaucous, adult wood; finely barked.

*Branching.*—2 main stems per 1 quart container, 1 to 3 lateral branches per main stem, average of 5 tertiary branches per lateral stem.

*Stem size.*—Average of 2 mm in width, up to 10 cm in length.

*Thorns.*—Shape triangular, aspect slightly downward, base oval, average of 5 in number per stem per 8 cm length stem, average of 5 mm in length with a base 3 mm in length and 1 mm in width, 178A in color.

Foliage description:

*Leaves.*—Compound, division is odd-pinnate, arrangement is alternate, average of 5.5 cm in length and 4 cm in width, internode length is an average of 2 cm.

*Leaflets.*—5 to 7, average of 2.5 cm in length and 1.8 cm in width, ovate to oval in shape, cuneate to rounded base, acute apex, serrate margins, color; emerging leaves upper surface; a blend of 144A and 178A, color; emerging leaves lower surface 144B suffused with 178A, young leaves upper surface 137A, margins 187A, young leaves lower surface 138A suffused with 187A, mature leaves upper surface 137A to 137B, mature leaves lower surface; 138B, pinnately veined (not conspicuous), surface glabrous and glossy on upper surface and glabrous and dull on lower surface.

*Rachis.*—Average of 3 cm in length and 1 mm in diameter, color; upper surface 144A suffused with 178A, lower surface 144A, rounded in shape with a center groove on upper surface, surface is smooth on upper and lower surface with a few sparse long hairs on upper surface.

*Stipules.*—Aspect outward, adnate to petiole, average of 9 mm in length and 2 mm in width, color upper and lower surface; 144B suffused with 178B, glabrous upper and lower surface.

*Petioles and petiolules.*—Petioles; an average of 1 cm in length and 1 mm in diameter, petiolules; an average of 1 mm in length and 0.8 mm in diameter, petioles and petiolules; color of mature leaves upper surface; 144B suffused with 178B, color of mature leaves lower surface; 144B, slightly pubescent upper surface, glabrous lower surface.

Inflorescence description:

*Inflorescence type.*—1 to 2 flowers per lateral branch, semi-double flowers.

*Flower number.*—Continuously produced throughout the growing season, 1 to 2 per lateral stem at one time.

*Flower fragrance.*—Faint rose scent.

*Flower longevity.*—5 to 8 days, depending on temperature and sunlight exposure.

*Flower type.*—Semi-double, rosette in form.

*Flower size.*—Average of 3.5 cm in diameter and 2.5 cm in depth (including hypanthium).

*Peduncles.*—Round in shape, average of 3 cm in length and 2 mm in diameter, surface is dull with sparse hairs, 144A in color.

*Bracts.*—None observed.

*Flower buds.*—Ovate in shape, an average of 2.5 cm in length and 1.7 cm in width prior to opening, color 58A with sepal portion a blend of 138B and 138C.

*Sepals.*—5, triangular in shape, margin entire or with 5 to 6 small leaflets, color of upper surface; a blend of 138B and 138C, color of lower surface; 138B, suffused or mottled with 59A, an average of 1.8 cm in length and 7 mm in width, aristate apex, truncate base (lower 2 cm fused), upright to reflexed on mature flowers, pubescent on upper and lower surface.

*Petals.*—An average of 12 per flower, drop readily and cleanly, rounded to broadly obcordate in shape, upper and lower surface glabrous, margin entire and very slightly undulated, base rounded to broadly cuneate, apex is rounded-slightly acute with occasional small notch, average of 1.7 cm in length and width, color; opening and fully open lower surface 58A, base 4B, fading flowers upper and lower surface a blend of 58C and 58D, base 4B.

*Hypanthium.*—Average of 7 mm in diameter and depth, urn-shaped, glossy surface, color; 137C, suffused with 183A, receptacle is disk shaped, 5 mm in diameter and 145D in color.

*Pistils.*—Average of 40 per flower, stigma is an average of 0.5 mm in diameter and 154D in color, style is an average of 2.5 mm in length and a blend of 145D and 59C in color, ovaries are oblong in shape, about 2.5 mm in length, pubescent surface.

*Stamens.*—Average of 60, filaments are an average of 4 mm in length and 145D in color, anthers are an average of 2.5 mm in length, an average of 1.5 mm in width and 11A in color, pollen is abundant in quantity and 17B in color.

*Hips.*—Globose to slightly conical in shape, an average of 1.7 cm in width and height, color; a blend of 138A and 138B and suffused with 187A to 187C, surface is dull.

It is claimed:

1. A new and distinct cultivar of *Rosa* plant named 'SFROSA154' as herein illustrated and described.

* * * * *